United States Patent [19]

Kamrat

[11] Patent Number: 4,571,075

[45] Date of Patent: Feb. 18, 1986

[54] MEASURING WINDOW FOR A PROCESS REFRACTOMETER

[75] Inventor: Esko Kamrat, Vantaa, Finland

[73] Assignee: K-Patents Oy, Helsinki, Finland

[21] Appl. No.: 515,485

[22] Filed: Jul. 20, 1983

[30] Foreign Application Priority Data

Aug. 30, 1982 [FI] Finland ................................. 822993

[51] Int. Cl.[4] ...................... G01N 21/17; G01N 21/41

[52] U.S. Cl. ..................................... 356/136; 356/128

[58] Field of Search ............... 356/128, 135, 136, 137; 350/287

[56] References Cited

U.S. PATENT DOCUMENTS 3,628,867 12/1971 Brady ................................. 356/136

FOREIGN PATENT DOCUMENTS 113777 5/1898 Fed. Rep. of Germany .
1383146 11/1964 France ............................... 356/136
1151301 7/1969 United Kingdom .
2085611 4/1982 United Kingdom .

*Primary Examiner*—R. A. Rosenberger
*Assistant Examiner*—Michael Vollero
*Attorney, Agent, or Firm*—Young & Thompson

[57] ABSTRACT

The invention relates to a measuring window for a process refractometer. Process refractometers are commonly used in the industry for continuous measurement of the concentration of a solution. The wall of the refractometer facing the process solution is provided with a window which must satisfy the requirement that the passage of light rays satisfies certain criteria, that the sealing is reliable, that the fastening is firm and that the wall facing the process and the window form a planar surface. The transparent portion of the window according to the invention comprises a roof prism embedded in a V-shaped groove in the process wall. Each wall of the V-groove is provided with a sealing abutting against the prism, and the third side of the prism forms a continuous plane with the process wall.

2 Claims, 3 Drawing Figures

MEASURING WINDOW FOR A PROCESS REFRACTOMETER

The invention relates to a measuring window for a process refractometer. Process refractometers are commonly used in the industry for continuous measurement of the concentration of a solution. The measuring method is based on keeping the solution to be measured in contact with the measuring window of the process refractometer and on illuminating the interface through the window with a light beam containing divergent light rays. The critical angle of total reflection from the interface between the solution and the window, which is a measure of the concentration of the solution, is determined from the reflected light by means of a photoelectric analyser.

Both the light rays coming from a light source and leaving to the analyser ought to penetrate the surfaces of the window as perpendicularly as possible. However, on the other side of the window facing the process, the angle of the light rays to the surface normal of the window ought to be rather great. This implies that the window cannot be a conventional window in which the interfaces of the transparent element comprise two planes parallel with each other, but the transparent part of the window must be prismatic.

Because the window also serves to protect the light source and the photoelectric analyser against the process solution, the sealing must be reliable and pressure-proof. It is of advantage to arrange the interface between the window and the process liquid in the same plane as the surface of the process wall because the surface of the window then more readily remains clean. If the surface of the window is not clean, errors in the measurement of the concentration will occur. In addition, the window must be firmly secured because even a small movement will cause a considerable measuring error.

No window construction is previously known which could combine all above-mentioned advantageous properties. Of the known constructions, the most common ones use as transparent element a prism having a cross-sectional shape of a symmetrical trapezoid. Such a construction is shown, for example, in the U.S. Pat. No. 3,751,168 and The Electron Machine Corporation Brochure: "Modell SSR-72 Critical Angle Refractometer". In this case the light source is located on one side of the axis of symmetry and the photoelectric analyser on the other side thereof. The rays from the light source strike at right angles the longer parallel side, are reflected from the oblique side on the same side of the axis of symmetry and meet the shorter parallel side forming the interface of the window facing the process. The light reflected from the interface is further reflected from the other oblique side perpendicularly through the longer parallel side to the photoelectric analyser. The process wall is provided with a conical hole which tapers towards the process and in which the prism is arranged. However, in order to keep the prism and the sealing in place, the hole is not entirely conical, but on the process side is provided a tapered section which forms an edge supporting the prism and the sealing. This means that the surface of the prism facing the process is located in a recess at a lower level than the surface of the process wall. From the U.S. Pat. No. 3,628,867 is known a construction which uses a prism of the same shape but in which the prism and the process wall form a straight plane. In this construction, the hole in the process wall is conical throughout the wall, and the sealing comprises a thin Teflon membrane shaped to match the wall of the hole. This construction suffers from the drawback that the window is not fixedly secured but floats on top of the membrane. In addition, the sealing is unreliable.

In the construction according to the invention, the plane of the window facing the process and the process wall form a planar surface, but nevertheless the transparent element of the window is so rigidly secured that it is unable of swinging or rotating. In addition, both sealings are located between planar surfaces so that the best possible standard sealing can be chosen. Differing from the previously known constructions, the process pressure presses the transparent element of the window against the sealing which improves the safety. In addition, it is of advantage that the passage of light takes place without any additional reflections within the prism because the condition of additional reflection surfaces influences the measuring result.

Figure 2:
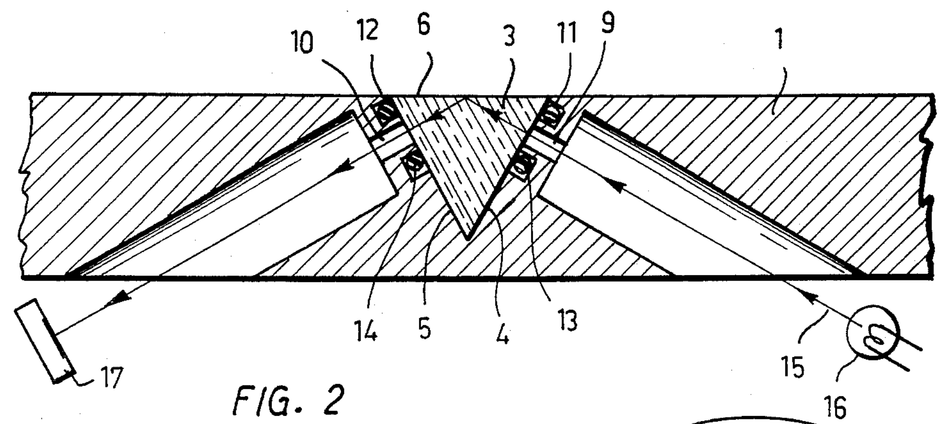
FIGS. 2 and 3 illustrate the measuring window of the process refractometer according to the invention.
Figure 1:
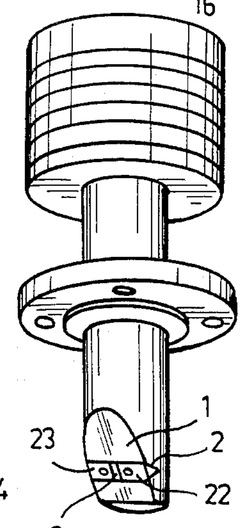
FIG. 1 is a general view of a process refractometer.
Figure 3:
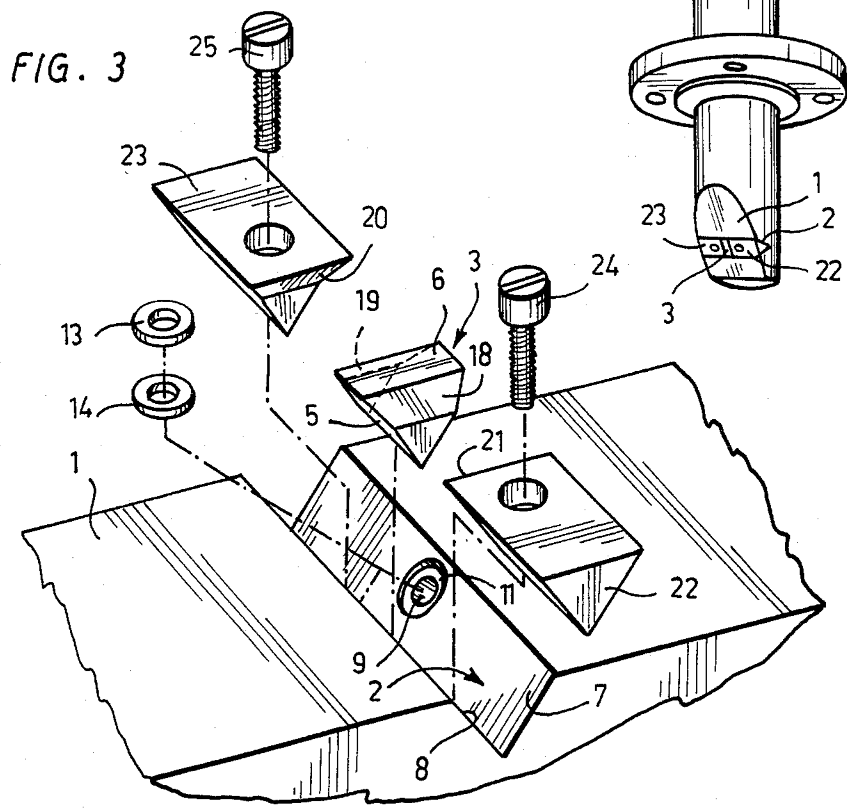

The process wall 1 is on the side facing the process provided with a V-shaped groove 2. The transparent element of the measuring window comprises a prism 3 made of spinel having a cross-sectional shape of a symmetrical triangle which is arranged in the V-groove so that the two optical surface 4, 5 of the prism abut against each wall 7, 8 of the V-groove 2. The third optical surface 6 of the prism forms a continuous straight plane with the process wall 1. Each wall of the V-groove is provided with a hole 9, 10 surrounded by a sealing groove 11, 12. An O-ring 13, 14 is used as sealing. The optical system functions so that light 15 emitted from the light source 16 passes through the hole 9 on one side 7 of the V-groove 2 into the prism 3 and falls on the side 6 of the prism facing the process. The light reflected therefrom leave the prism 3 through the hole 10 on the other side 8 of the V-groove 2 towards a photoelectric analyser 17. The fastening of the prism 3 is arranged so that material is worked from the opposite edges of the side 6 of the prism facing the process so as to form two oblique planes 18, 19 against which the corresponding planes 20, 21 at one end of fastening elements 22, 23 of triangular cross-section are pressed. The fastening elements 22, 23 and their planes 20, 21 are made so that, when they are fastened to the process wall 1 by means of screws 24, 25, they lock the prism 3 in place in the V-groove and, at the same time, form a planar surface with the process wall 1.

What I claim is:

1. A measuring window for a process refractometer including a V-shaped groove in the process wall, a prism of triangular cross section in the V-shaped groove with one side flush with one side of the process wall, there being a hole for the passage of light in both sides of said V-shaped groove, each hole opening also through the side of the wall opposite said one side, and a sealing ring surrounding each hole and in sealed relation both with the prism and with said wall.

2. A measuring window as claimed in claim 1, the prism having diagonal surfaces on each side of said flush side of the prism, and a fastening element of triangular cross section on each side of the prism, the fastening elements fitting into the V-shaped groove and each having one side flush with said one side of the process wall, each fastening element having a protruding part that meets with and presses against a said diagonal surface of the prism.

* * * * *